United States Patent [19]

Gentelia et al.

[11] Patent Number: 5,496,313
[45] Date of Patent: Mar. 5, 1996

[54] SYSTEM FOR DETECTING PENETRATION OF MEDICAL INSTRUMENTS

[75] Inventors: John S. Gentelia, Madison; Ernesto G. Sevilla, Herkimer, both of N.Y.

[73] Assignee: Conmed Corporation, Utica, N.Y.

[21] Appl. No.: 308,913

[22] Filed: Sep. 20, 1994

[51] Int. Cl.⁶ .................................................. A61B 17/36
[52] U.S. Cl. .................. 606/34; 606/41; 606/45; 606/46; 604/164; 604/264
[58] Field of Search .................. 606/32–34, 41, 606/42, 45–50, 185, 167, 170; 604/164, 264, 21, 22, 156, 157, 158

[56] References Cited

U.S. PATENT DOCUMENTS

| | | | |
|---|---|---|---|
| 5,300,070 | 4/1994 | Gentelia et al. | 606/45 |
| 5,344,420 | 9/1994 | Hilal et al. | 606/45 |
| 5,380,321 | 1/1995 | Yoon | 606/41 |
| 5,429,686 | 7/1995 | Shikhnan et al. | 606/41 |

Primary Examiner—Stephen C. Pellegrino
Assistant Examiner—Michael Peffley
Attorney, Agent, or Firm—Larson and Taylor

[57] ABSTRACT

A device is provided for use with a medical instrument including a tip which is designed to penetrate the wall of an internal cavity (e.g., the abdomen) of a patient, for detecting when that tip penetrates through the wall. The device includes a source of a medium frequency detection signal and circuitry for coupling the signal to the tip of the medical instrument. The circuitry includes a transformer forming a high Q resonant circuit having an initial value of Q when the medical instrument is not in use. A return path for the signal provides that, in use of the instrument, a circuit is completed through the resonant circuit such that when the tip contacts patient tissue the initial Q of the resonant circuit changes and when the tip penetrates through the patient tissue of the Q of the circuit is restored to the initial value thereon. A detector detects the change in Q of the resonant circuit and produces an output when changed Q is restored to the initial value thereof so as to indicate that the tip has penetrated through the patient tissue.

20 Claims, 2 Drawing Sheets

5,496,313

SYSTEM FOR DETECTING PENETRATION OF MEDICAL INSTRUMENTS

CROSS REFERENCE TO RELATED APPLICATION

This application contains subject matter related to that disclosed in the following U.S. applications: U.S. application Ser. No. 08/069,359, filed Jun. 6, 1993, now U.S. Pat. No. 5,436,566 which is a continuation-in-part of U.S. application Ser. No. 08/009,598, filed Jan. 27, 1993, now U.S. Pat No. 5,432,459 which is a continuation-in-part of U.S. Ser. No. 07/901,024, filed Jun. 19, 1992, now U.S. Pat. No. 5,300,070 which is a continuation-in-part of U.S. Ser. No. 07/853,149, filed Mar. 17, 1992.

1. Field of the Invention

The present invention relates to systems for detecting when the tip of a medical instrument such as a trocar or an insufflation needle penetrates a cavity wall of a patient such as the wall of the abdominal cavity.

2. Background of the Invention

As discussed in the above-identified applications, there are a number of medical situations wherein it is useful and, in some instances where safety is of the utmost concern, necessary for a surgeon or those assisting him to know precisely when a medical instrument penetrates the wall of the cavity involved in the operation (e.g., the peritoneum) so that further penetration, and possible attendant injury to the patient, can be avoided. For example, as described in these applications, it is desirable when using the electrosurgical trocar disclosed in patent application Ser. No. 07/853,149 and 07/901,024 to shut down the associated electrosurgical generator when the tip of the cutting element of the trocar penetrates the body cavity wall. Another example of where this type of detection is important or critical is detecting when an insufflation needle for insufflating the abdomen enters the abdominal cavity.

SUMMARY OF THE INVENTION

In accordance with a preferred embodiment thereof, the present invention comprises, in combination, a medical instrument including a tip which is designed to penetrate the wall of an internal cavity of a patient, and a device for detecting when the tip penetrates through said wall, the device comprising: a source of a detection signal; means for coupling the signal to the tip of said medical instrument, the coupling means including a high Q resonant circuit having an initial value of Q when the medical instrument is not in use; means for providing a return path for the signal so that, in use of the instrument, a circuit is completed through said resonant circuit such that, when the tip contacts patient tissue, the initial Q of the resonant circuit changes and when the tip penetrates through the patient tissue, the Q of the circuit is restored to the initial value thereto, and detector means for detecting the change in Q of said resonant circuit and for producing an output when the changed Q is restored to the initial value thereof so as to indicate that the tip has penetrated through the patient tissue.

In one important implementation, the medical instrument comprises an electrosurgical instrument connected to an electrosurgical generator and the output produced by the detector means provides for cutting off of the electrosurgical generator. Preferably, in this implementation, the resonant circuit includes a capacitor of a value high enough to ensure that substantially all of the electrosurgical current flows through the capacitor.

Advantageously, the device further comprises indicator means for, responsive to receiving said output from the detector means, providing an indication that the tip has penetrated through the patient tissue. In one preferred embodiment, the indicator means comprises a light indicator such as a blinking red light. Alternatively, or additionally, the indicator means can comprise an alarm device such as a buzzer, beeper, or the like.

In an advantageous implementation for electrosurgical applications, the frequency of the detection signal produced by the source is a medium frequency, advantageously between 5 and 10 kHz, although other frequencies can be used. Advantageously, the amplitude of the signal produced by said source is less than 1 volt peak to peak, although higher amplitudes can be employed.

The coupling means preferably includes a high Q resonant transformer and a conductor connected to the tip, the transformer including a secondary winding connected in the series with the conductor and having a capacitor connected thereacross so as to form the resonant circuit, and a primary winding connected in series with the source. Advantageously, a filtering means is provided for filtering out unwanted signals so as to prevent said unwanted signals from passing to said detector means. In an implementation wherein the medical instrument is an electrosurgical device driven by an electrosurgical generator, the filtering means comprises means for filtering out any electrosurgical current coupled back to the detector means and for filtering out noise from other sources.

In one embodiment, the detector means comprises a current detector means, connected in a series circuit with the source and the secondary winding, for producing an output signal related to the current flow in the series circuit, and a logic circuit, responsive to the magnitude of said current flow, for producing said output. In another advantageous embodiment, the detector means comprises a synchronous amplitude detector.

In one preferred embodiment, the means for providing said return path comprises a grounding pad adapted to be applied to a patient.

In another preferred implementation, the invention is used with a mechanical medical instrument such as a mechanical trocar or an insufflation needle. In this implementation, an insulated conductor is incorporated into the body of the instrument and an end of the conductor is exposed at a site near the tip of the instrument. A return path can be provided through the body of the instrument or through a grounding pad.

Other features and advantages of the invention will be set forth in, or apparent from, the following detailed description of preferred embodiments of the invention.

DESCRIPTION OF THE PREFERRED EMBODIMENTS

Figure 1:
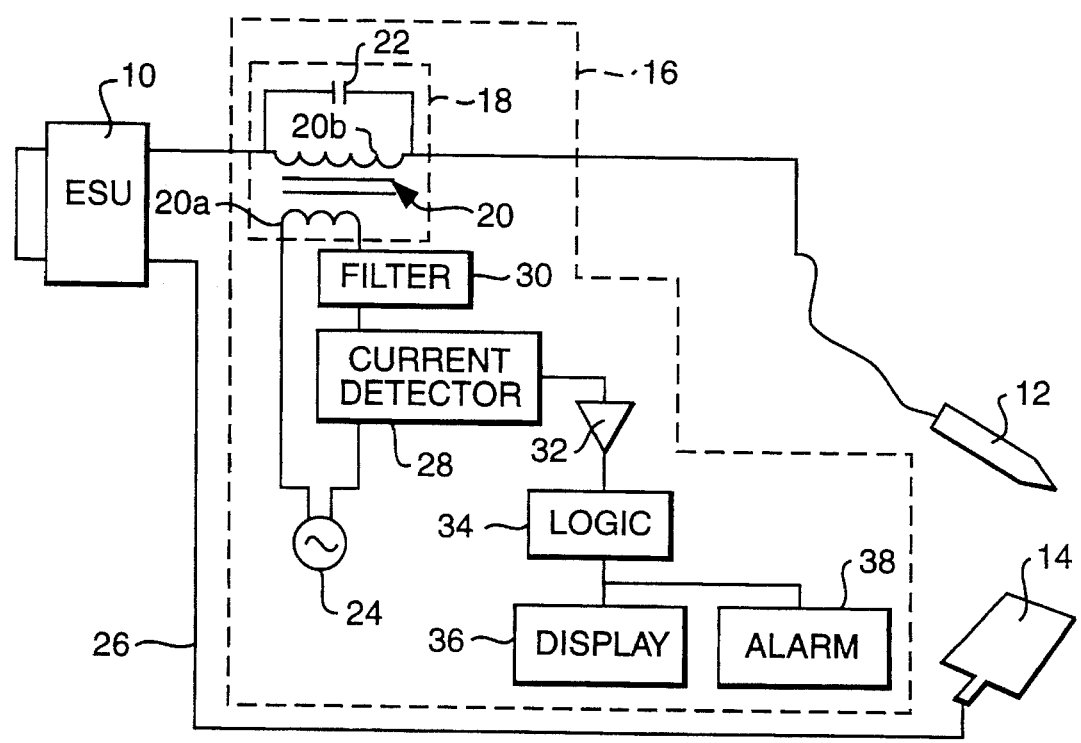
FIG. 1 is a schematic circuit diagram of one preferred embodiment of the detector system of the invention.

Referring to FIG. 1, a first embodiment of the invention is shown. In this embodiment, the detection system of the invention is incorporated in an electrosurgical system including an electrosurgical generator or unit (ESU) 10, an electrosurgical cutting instrument 12, and a ground return pad or electrode 14. The instrument 12 can be an electrosurgical trocar such as is disclosed in the above-identified applications, a conventional electrosurgical cutting device or any other electrosurgical device, the tip of which, in use, penetrates the wall of an internal cavity of a patient. As is, of course, well known, the ground return pad 14 is applied to the body of the patient and provides a return path for electrical current in the circuit comprising ESU 10 and electrosurgical instrument 12.

The detector of the invention is generally denoted 16 and incudes a high Q resonant transformer unit 18 comprising a transformer 20 including a primary winding 20a and a secondary winding 20b and having a capacitor 22 connected across secondary winding 20b. The primary winding 20a of the high Q resonant transformer unit 18 is connected in series with a signal source 24 and the function of transformer unit 18 is to couple a low amplitude, medium frequency signal produced by source 24 to the electrosurgical instrument 12.

The electrosurgical instrument 12 is constructed such that the electrical signal appears at the tip of the instrument and this tip is insulated from the instrument body so that signal current flows from the tip of instrument 12 through a signal return lead 26 connected to the standard electrosurgical grounding pad 14. Suitable arrangements for providing this are shown in the applications referenced hereinabove.

In an exemplary, preferred embodiment, the amplitude of the signal produced by source 24 is less than about 1 volt peak to peak but other, higher amplitudes can be used. The frequency of the signal produced by source 24 is chosen so as to be distinct from that of the ESU 10 and to be high enough for the impedance between the grounding pad 12 and the skin of the patient to be reasonably small, yet not so high as to cause significant leakage effects. A frequency range of between 5 and 10 kilohertz (kHz) is preferred although other frequencies can be used. In the specific implementation under consideration, i.e., one wherein the detector is used in an electrosurgical application, the value of capacitor 22 is chosen to be relatively large so that most of the electrosurgical current flows through capacitor 22 and thus is not coupled to the detector circuit.

In common with the systems described in the patent applications referenced above, the detector of the invention generally relies on detection of current flow and to this end, the detector circuit including transformer 20 and source 24, also includes a series connected current detector 28. Normal filtering techniques, represented by a filter 30 connected in series with current detector 28, are used to remove any of the electrosurgical current that is coupled back to the detector 28 as well as extraneous noise from other sources. The output of current detector 28 is coupled through an amplifier 32 to a logic circuit 34 the output of which is used to activate a display 35 (e.g., an indicator lamp) and/or an alarm 38 (e.g., a buzzer or beeper). A change in current detected by detector 28 which indicates that the current flow has been restored to the initial thereof causes a logic level to be generated that is indicative of the completion of the insertion of the instrument 12.

In operation, the Q of the tuned or resonant circuit of transformer unit 18 will be degraded from the initial value thereof when the instrument 12 is out of contact with the patient to a new, different value when the tip of the instrument 12 is in contact with patient tissue, whether this tissue be fat or muscle, at the initial stage of the insertion of the instrument 12 into a body cavity such as the abdominal cavity. This degradation in the value of Q results in change in the current flow detected by current detector 28. When the tip of the instrument enters into the cavity, the resonant circuit regains, or returns to, its initial Q and this is detected by current detector 28, causing a logic level to be generated by logic circuit 34 indicating completing of the insertion, i.e., indicating that the tip has cleared the tissue and entered the cavity. The output level produced logic circuit 34 causes activation of display 36 and alarm 38. It will, of course, be appreciated that the entry of the tip can be signaled in any suitable manner and that an alarm such as a buzzer or beeper and light display or indication (e.g., the turning on of blinking red light) are merely examples, and that, further, either or both can be used as desired. Moreover, the output of logic circuit 34 can additionally, or alternatively, be used to shut down the generator of ESU 10.

Figure 2:
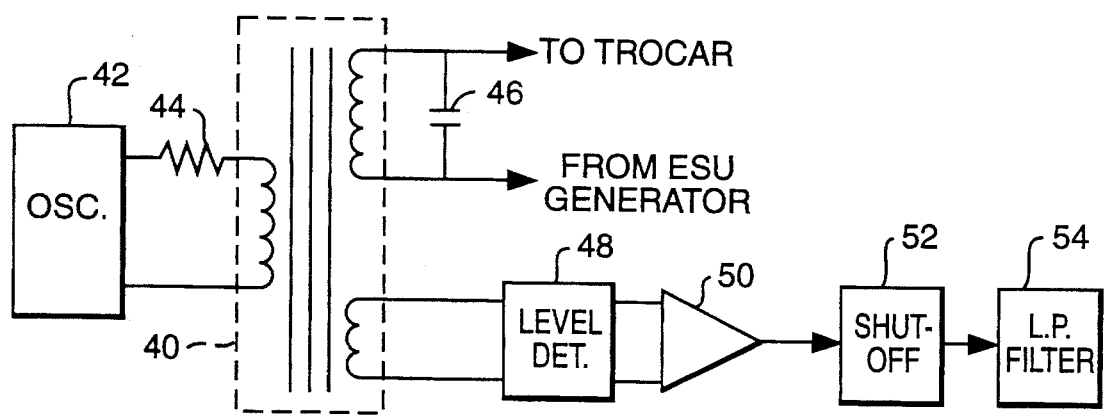
FIG. 2 is a schematic circuit diagram of a further embodiment similar to that of FIG. 1.

Referring to FIG. 2, an embodiment similar to that of FIG. 1 is shown. A transformer 40 includes a primary winding 40a connected to an oscillator 42 through a resistor 44 and a first secondary winding 40b having a capacitor 46 connected thereacross to form a high Q tuned circuit corresponding to that discussed above. The leads from winding 40b are respectively connected to the trocar (not shown) and to (from) the ESU generator (not shown) as discussed above. A second secondary winding 40c is connected through a low filter 48, an amplifier 50 and a level detector 52 to, in this example, a shutoff circuit 54. The operation of the embodiment of FIG. 2 is generally the same as described above. As noted above, the tuned winding 40b is connected in series with the lead from the ESU (not shown) and to the trocar (not shown) and the return path is provided through the ground pad (not shown) as in FIG. 1.

Figure 3:
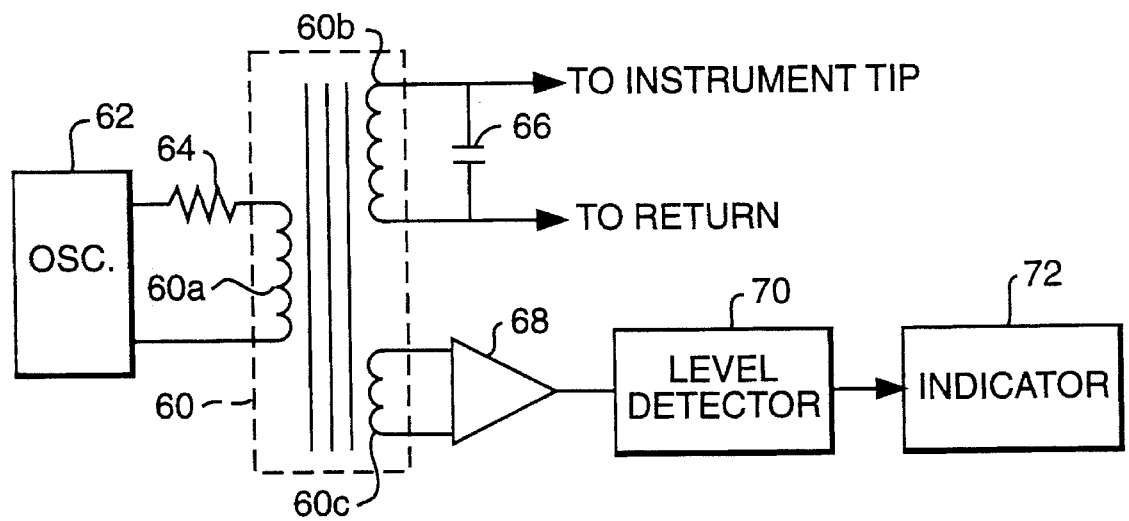
FIG. 3 is a further embodiment adapted for use with a mechanical instrument such as a mechanical trocar or insufflation needle.

As discussed hereinabove, the invention is also applicable to other medical devices wherein it is desired to know that penetration has occurred. For example, the invention can be used to detect, electronically, when an insufflation needle has entered the abdominal cavity. In such an application the circuit would be generally the same as shown in FIGS. 1 and 2 but with the ESU eliminated. An exemplary embodiment is shown in FIG. 3 which is similar to that of FIG. 2. A transformer 60 includes a primary winding 60a connected to an oscillator 62 through a resistor 64 and the high Q tuned circuit is formed by a secondary winding 60b and a capacitor 66. The leads of winding 60b are connected to the instrument tip and to a return path, as illustrated. Detection is provided by a second secondary winding 60c, an amplifier 68, a level detector 70 and an indicator 72.

Figure 4:
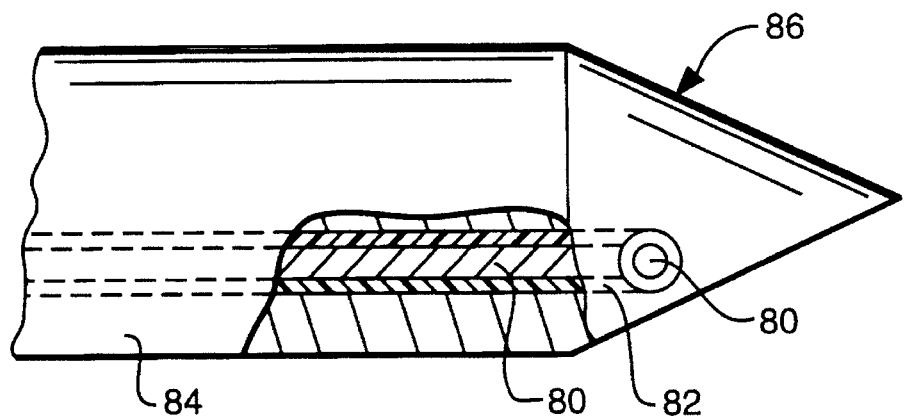
FIG. 4 is a side elevational view, partially broken away, of the tip of a mechanical instrument as adapted to include a sensing conductor.

A ground pad corresponding to pad 14 could be retained in a preferred embodiment of this implementation although a return path could also be provided in a different manner, such as, for example, by providing a bipolar assembly wherein a return lead or conductor is located in the body of the trocar or needle along with a signal lead at the tip discussed below. Regarding the latter and referring to FIG. 4, it will be appreciated that when the detection system of the invention is applied to a mechanical (as opposed to electrosurgical) medical instrument such as a mechanical trocar or insufflation needle, the instrument must be modified so that the electrical detection signal appears at the tip of the instrument. This is shown in FIG. 4 wherein a lead or conductor 80 is insulated by an outer insulating covering 82 from the body 84 of the instrument 86. As illustrated, the end of conductor 80 is exposed.

Although the present invention has been described relative to specific exemplary embodiments thereof, it will be understood by those skilled in the art that variations and modifications can be effected in these exemplary embodiments without departing from the scope and spirit of the invention.

What is claimed is:

1. In combination, a medical instrument including a tip which is designed to penetrate the wall of an internal cavity of a patient, and a device for detecting when the tip penetrates through said wall, said device comprising: a source of a detection signal; means for coupling said signal to the tip of said medical instrument, said coupling means including a high Q resonant circuit having an initial value of Q when the medical instrument is not in use; means for providing a return path for said signal so that, in use of the instrument, a circuit is completed through said resonant circuit such that when said tip contacts patient tissue the initial Q of the resonant circuit changes and when the tip penetrates through the patient tissue the Q of the circuit is restored to said initial value; and detector means for detecting the change in Q of said resonant circuit and for producing an output when changed Q is restored to the initial value thereof so as to indicate that said tip has penetrated through the patient tissue.

2. The combination as claimed in claim 1 wherein said medical instrument comprises an electrosurgical generator and wherein said output produced by said detector means provides for cutting off of said electrosurgical generator.

3. The combination as claimed in claim 1 further comprising indicator means for, responsive to receiving said output from said detector means, providing an indication that said tip has penetrated through the patient tissue.

4. The combination as claimed in claim 3, wherein said indicator means comprises a light indicator.

5. The combination as claimed in claim 1 wherein the frequency of said signal produced by said source is a medium frequency signal.

6. The combination as claimed in claim 5 wherein the frequency of said signal produced by said source is between 5 and 10 kHz.

7. The combination as claimed in claim 1 wherein the amplitude of said signal produced by said source is less than 1 volts peak to peak.

8. The combination as claimed in claim 1 wherein said resonant circuit of said coupling means comprises a high Q resonant transformer and said coupling means further comprises a conductor connected to said tip, said transformer including a secondary winding connected in series with said conductor and having a capacitor connected there across so as to form said resonant circuit, and a primary winding connected in series with said source.

9. The combination as claimed in claim 8 further comprising filtering means for filtering out unwanted signals so as to prevent said unwanted signals from passing to said detector means.

10. The combination as claimed in claim 9, wherein said medical instrument comprises electrosurgical medical instrument connected to an electrosurgical generator, said filtering means comprises means for filtering out any electrosurgical current coupled back to the detector means and for filtering out noise from other sources.

11. The combination as claimed in claim 8, wherein said detector means comprises a current detector means, connected in a series circuit with said source and said secondary winding, for producing an output signal related to the current flow in said series circuit, and a logic circuit, responsive to the magnitude of said current flow, for producing said output.

12. The combination as claimed in claim 1, wherein said detector means comprises a synchronous amplitude detector.

13. The combination as claimed in claim 1 wherein said means for providing said return path comprises a grounding pad adapted to be applied to a patient.

14. The combination as claimed in claim 1 wherein said medical instrument comprises an electrosurgical device including an electrosurgical generator, and wherein said resonant circuit includes a capacitor of a value high enough to ensure that substantially all the electrosurgical current flows through said capacitor.

15. The combination as claimed in said claim 1 wherein said transformer includes a primary winding and said source comprises an oscillator connected to said primary winding.

16. The combination as claimed in claim 15 wherein said transformer includes first and second secondary windings, said first transformer secondary winding having a capacitor connected there across to form said Q resonant circuit and said second transformer secondary winding being connected to said detector means.

17. The combination as claimed in claim 16 wherein said instrument comprises an electrosurgical instrument and said device includes a low pass filter connected to said second secondary winding.

18. The combination as claimed in claim 1 wherein said instrument comprises a mechanical instrument and said mechanical instrument includes a insulated conductor incorporated therein and an end exposed at least near said tip.

19. The combination as claimed in claim 18 wherein said detector means comprises a level detector.

20. In combination, an electrosurgical instrument connected to an electrosurgical generator and including a tip which is designed to penetrate the wall of an internal cavity of a patient, and a device for detecting when the tip penetrates through said wall, said device comprising: a source of a detection signal; means for coupling said signal to the tip of said instrument, said coupling means including a high Q resonant circuit having an initial value of Q when the instrument is not in use; means for providing a return path for said signal so that, in use of the instrument, a circuit is completed through said resonant circuit such that when said tip contacts patient tissue the initial Q of the resonant circuit changes and when the tip penetrates through the patient tissue the Q of the circuit is restored to said initial value; and detector means for detecting the change in Q of said resonant circuit and for producing an output, when the changed Q is restored to the initial value thereof indicating that said tip has penetrated through the patient tissue, for cutting off said electrosurgical generator.

* * * * *